(12) United States Patent
Sudhir et al.

(10) Patent No.: US 9,839,537 B2
(45) Date of Patent: Dec. 12, 2017

(54) BIORESORBABLE POLYMER SCAFFOLD TREATMENT OF CORONARY AND PERIPHERAL ARTERY DISEASE IN DIABETIC PATIENTS

(71) Applicant: Abbott Cardiovascular Systems Inc., Santa Clara, CA (US)

(72) Inventors: Krishnankutty Sudhir, Santa Clara, CA (US); Wai-Fung Cheong, Los Altos, CA (US); Lee Clark, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 271 days.

(21) Appl. No.: 13/789,280

(22) Filed: Mar. 7, 2013

(65) Prior Publication Data

US 2013/0238078 A1    Sep. 12, 2013

Related U.S. Application Data

(60) Provisional application No. 61/607,977, filed on Mar. 7, 2012.

(51) Int. Cl.
| | |
|---|---|
| A61F 2/82 | (2013.01) |
| A61F 2/958 | (2013.01) |
| A61L 31/16 | (2006.01) |
| A61F 2/915 | (2013.01) |
| A61L 31/06 | (2006.01) |
| A61L 31/14 | (2006.01) |

(52) U.S. Cl.
CPC .............. *A61F 2/82* (2013.01); *A61F 2/915* (2013.01); *A61F 2/958* (2013.01); *A61L 31/06* (2013.01); *A61L 31/148* (2013.01); *A61L 31/16* (2013.01); *A61F 2002/91566* (2013.01); *A61F 2230/0054* (2013.01)

(58) Field of Classification Search
CPC ......................................................... A61F 2/82
USPC ....................................................... 623/1.38
See application file for complete search history.

(56) References Cited

U.S. PATENT DOCUMENTS

| | | | |
|---|---|---|---|
| 5,425,739 | A | 6/1995 | Jessen |
| 5,500,013 | A | 3/1996 | Buscemi et al. |
| 6,762,418 | B2 | 7/2004 | Lambert et al. |
| 8,002,817 | B2 | 8/2011 | Limon |
| 8,182,890 | B2 | 5/2012 | Zheng et al. |
| 8,207,240 | B2 | 6/2012 | Lambert et al. |
| 8,568,471 | B2 | 10/2013 | Trollsas et al. |
| 2002/0082679 | A1 | 6/2002 | Sirhan et al. |
| 2003/0074049 | A1 | 4/2003 | Hoganson et al. |
| 2005/0124619 | A1* | 6/2005 | Timmer et al. ............... 514/241 |
| 2007/0202046 | A1 | 8/2007 | Dave |

(Continued)

FOREIGN PATENT DOCUMENTS

DE        10223399        12/2003

OTHER PUBLICATIONS

U.S. Appl. No. 13/403,709, filed Feb. 23, 2012, Hossainy et al.

(Continued)

*Primary Examiner* — Matthew Schall
(74) *Attorney, Agent, or Firm* — Squire Patton Boggs (US) LLP

(57) ABSTRACT

Methods of treating coronary and peripheral artery disease in diabetic patients with bioresorbable polymer stents are described. The stents may include everolimus.

14 Claims, 12 Drawing Sheets

(56) References Cited

U.S. PATENT DOCUMENTS

| | | | |
|---|---|---|---|
| 2007/0275537 A1 | 11/2007 | Henson et al. |
| 2007/0280851 A1 | 12/2007 | Freeman et al. |
| 2007/0283552 A1 | 12/2007 | Gale et al. |
| 2008/0010947 A1 | 1/2008 | Huang et al. |
| 2008/0039545 A1 | 2/2008 | Muratoglu et al. |
| 2008/0275537 A1 | 11/2008 | Limon |
| 2008/0299002 A1 | 12/2008 | Freeman et al. |
| 2009/0074610 A1 | 3/2009 | Sabaria |
| 2009/0099652 A1 | 4/2009 | Granada et al. |
| 2009/0182415 A1 | 7/2009 | Wang |
| 2010/0004735 A1 | 1/2010 | Yang et al. |
| 2010/0198330 A1 | 8/2010 | Hossainy et al. |
| 2010/0198331 A1 | 8/2010 | Rapoza et al. |
| 2011/0190872 A1 | 8/2011 | Anukhin |
| 2013/0224255 A1 | 8/2013 | Hossainy et al. |
| 2013/0238078 A1 | 9/2013 | Sudhir et al. |
| 2013/0259921 A1 | 10/2013 | Hossainy |
| 2013/0261722 A1 | 10/2013 | Hossainy |
| 2013/0261723 A1 | 10/2013 | Stankus et al. |
| 2013/0317596 A1 | 11/2013 | Rapoza et al. |

OTHER PUBLICATIONS

U.S. Appl. No. 13/435,645, filed Mar. 30, 2012, Hossainy.
U.S. Appl. No. 13/436,303, filed Mar. 30, 2012, Hossainy.
U.S. Appl. No. 13/436,662, filed Mar. 30, 2012, Stankus et al.
Angioplasty Summit Abstracts/Oral, The Am. J. of Cardiology, Apr. 23-26, 2013, p. 23B.
Bosiers et al., "Coronary and endovascular applications of the Absorb™ bioresorbable vascular scaffold", Interv. Cardiol. 4(6), pp. 621-631 (2012).
Dudek et al., "Four-year clinical follow-up the ABSORB everolimus-eluting bioresorbable vascular scaffold in patients with de novo roronary artery disease: the ABSORB trial", EuroIntervention 7, pp. 1060-1061 (2011).
Everolimus Eluting Coronary Stent System Instructions for Use, 8 pgs (2012) www.abbottvascular.com.
FDA Summary of safety and effectiveness data (SSED), 46 pgs. (2011). http://www.accessdata.fda.gov/cdrh_docs/pdf11/P110019b.pdf.
Garratt et al., "Rationale and design of the TAXUS Liberté Post-Approval Study: Examination of patients receiving the TAXUS Liberté stent with concomitant prasugrel therapy in routine interventional cardiology practice", Am. Heart J. vol. 163, No. 2, pp. 143-149 (2012).
Miller "Abbott's Bioresorbable Stent Shows Durable Results in ABSORB Trial", The Gray Sheet, pp. 17-18, Mar. 2003.
New Data Reinforces Strong Clinical Performance of Abbott's Absorb™ Bioresorbable Vascular Scaffold, Press release, Mar. 11, 2013, 3 pgs.
"Stent retrievers: the future treatment of choice for endovascular recanalization in acute ischemic stroke" Interventional Cardiology, vol. 5, iss. 2, pp. 145-147 (2013).
U.S. Appl. No. 12/364,321, filed Feb. 2, 2009, Yunbing Wang.
ABSORB: Bioabsorbable Coronary Stents Successfully and Safely Deployed, downloaded from: www.tct2006.com/Dailies_TCT2006, Nov. 14, 2008, 1 pg.
Brugaletta et al., "Vascular Compliance Changes of the Coronary Vessel Wall After Bioresorbable Vascular Scaffold Implantation in the Treated and Adjacent Segments", Circ. J. vol. 76, (2012).
Compression Test, Materials Testing Solutions, downloaded from: www.instron.us/wa/applications/test_types/compressions.aspx, Nov. 14, 2008, 1 pg.
Costa et al., "Angiographic Results of the First Human Experience with Everolimus-Eluting Stents for the Treatment of Coronary Lesions (the Future I Trial)", The Am. J. of Card. vol. 95, pp. 113-116 (2005).
Fajadet et al., "Randomized, Double-Blind, Multicenter Study of the Endeavor Zotarolimus-Eluting Phosphorylcholine-Encapsulated Stent for Treatment of Native Coronary Artey Lessions", Circulation, pp. 798-806 (2006).
Gogas et al., "The dynamic vascular response at the proximal and distal edges following implantation of the ABSORB everolimues eluting bioresorbable vascular scaffold as assessed with virtual histology intravascular ultrasound", Abstract presented at EuroPCR, May 15-18, 2012.
Grube et al., "Six-and Twelve-Month Results from First Human Experience Using Everolimus-Eluting Stents with Bioabsorbable Polymer", Circulation, pp. 2168-2171 (2004).
Gussenhoven et al., "Intravascular Ultrasonic Imaging: Histologic and Echographic Correlation", Eur. Vasc. Surg. 3, pp. 571-576 (1989).
Kukreja et al., "Biodegradable drug eluting stents: invasive and non-invasive imaging", Euro Intervention 2, p. 403 (2006).
Lachowitzer "Assessing Radial Tests for Endovascular Implants", Medical Device Link, downloaded from: www.devicelink.com/grabber.php3?, Nov. 10, 2008, 4 pgs.
Markman, "Absorbable coronary stents", Lancet 369, pp. 1839-1840 (2007).
Meredith et al., "First-in-human study of the Endeavor ABT-578-eluting phosphorylcholine-encapsulated stent system in de novo native coronary artery lesions: endeavor I Trial", Clinical Research, EuroInterv. 1; pp. 157-164 (2005).
Mintz et al., "Arterial Remodeling after Coronary Angioplasty: A Serial Intravascular Ultrasound Study", Circulation 94, pp. 35-43 (1996).
Ormiston et al., "A bioabsorbable everolimus-eluting coronary stent system for patients with single de-novo coronary artery lesions (ABSORB): a prospective open-label trial", Lancet 371, pp. 899-907 (2008).
Ormiston et al., "First Serial Assessment at 6 mo. and 2 years of the Second Generation of Absorb Everolimus-eluting bio-resorbable vascular scaffold", Circ.: Cardiovascular Interventions 5, pp. 620-632 (2012).
Ormiston et al., "First-in-Human Impantation of a Fully Bioabsorbable Drug-Eluting Stent: The BVS Poly-L-Lactic Acid Everolimus-Eluting Coronary Stent", Catheterization and Cardiovascular Interventions 69: pp. 128-131 (2007).
Pietrzak et al., "Bioabsorbable Polymer Science for the Practicing Surgeon", The J. of Craniofacial Surgery vol. 8, No. 2, pp. 87-91 (1997).
Radial testing of Vascular Stents (ASTM F2079 and ASTM F2477), Materials Testing Solutions, downloaded from: www.instron.us/wa/solutions//Stents.aspx, Nov. 14, 2008, 1 pg.
Ramcharitar et al., "Fully Biodegradable Coronary Stents: Progress to Date", Am. J. of Card. Drugs vol. 8, No. 5, pp. 305-314 (2008) Abstract 2 pgs.
Serruys et al., "A bioabsorbable everolimus-eluting coronary stent system (ABSORB): 2-year outcomes and results from multiple imaging methods", Lancet 373, pp. 897-910 (2009).
Slottow et al., "Optical coherence tomography and intravascular ultrasound imaging of bioabsorbable magnesium stent degradation in porcine coronary arteries", Cardiovasc. Revascularization Medicine 9, pp. 248-254 (2008).
Stone et al., "A Polymer-Based, Paclitaxel-Elluting Stent in Patients with Coronary Artery Disease", The New England J. of Medicine, 350; 3, pp. 221-231 (2004).
Tanimoto et al., "Comparison of In Vivo Acute Stent Recoil Between the Bioabsorbable Everolimus-Eluting Coronary Stent and the Everolimus-Eluting Cobalt Chromium Coronary Stent: Insights From the ABSORB and SPIRIT Trails", Catheterization and Cardiovascular Interventions 70, pp. 515-523 (2007).
Tanimoto et al., "Late Stent Recoil of the Bioabsorbable Everolimus-Eluting Coronary Stent and its Relationship with Plaque Morphology", J. of Am. Col. of Cardiology vol. 52, No. 20, pp. 1616-1620 (2008).
Wood "ABSORBing the Details: 12-Month Results for Bioabsorbable, Everolimus-Eluting Stent", downloaded from: www.medscape.com/viewarticle/571705, Nov. 14, 2008, 16 pgs.
DCCT/EDIC. "Intensive Diabetes Treatment and Cardiovascular Disease in Patients with Type 1 Diabetes", New England Journal of Medicine. Dec. 2005; 353(25). pp. 2643-2653.

* cited by examiner

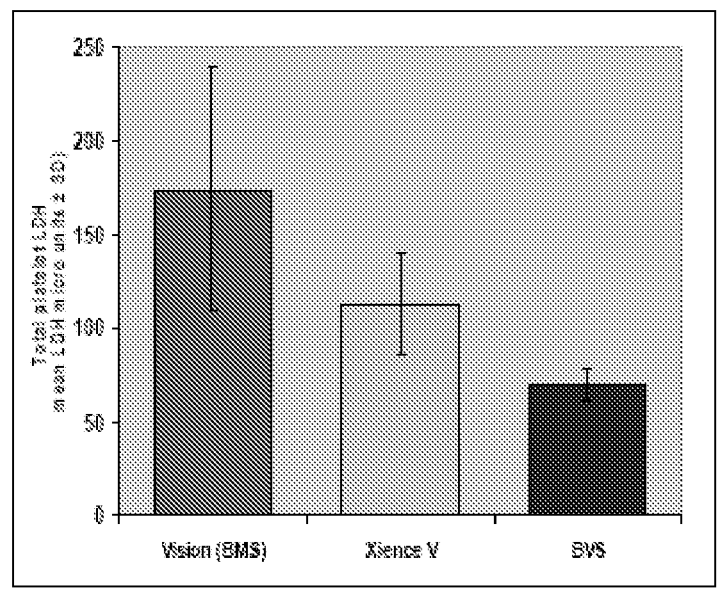
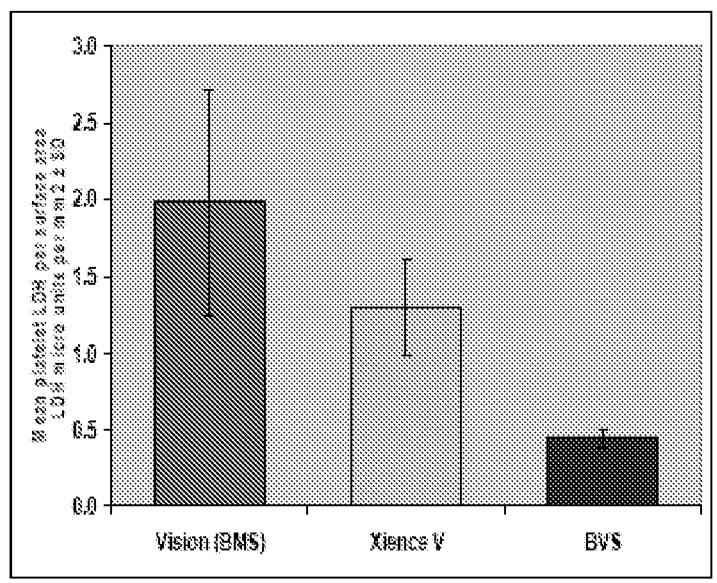
FIG. 5

Diabetes Incidence / Status

|  | Diabetics<br>N = 60 |
|---|---|
| Diabetes Mellitus Requiring Medication % | 88.3 |
| Diabetes Mellitus Requiring Insulin % | 18.3 |
| Diabetes Mellitus Requiring Oral Hypoglycemics % | 78.3 |
| Diabetes Mellitus Requiring Exercise or Diet Alone % | 8.3 |
| Diabetes Mellitus Requiring No Treatment % | 3.3 |

FIG. 6

Baseline Demographics

|  | Diabetics<br>N = 60 | Non-Diabetics<br>N = 241 | p value |
|---|---|---|---|
| Male (%) | 78.3 | 72.2 | 0.41 |
| Mean age (years) | 62 | 63 | 0.47 |
| Prior Cardiac Intervention on Target Vessel (%) | 6.7 | 5.8 | 0.76 |
| Previous MI (%) | 23.3 | 27.5 | 0.62 |
| Unstable Angina (%) | 25.0 | 26.6 | 0.87 |
| Dyslipidemia req. med. (%) | 73.3 | 68.5 | 0.53 |
| Hypertension req. med. (%) | 76.7 | 60.0 | 0.02 |
| Current smoker (%) | 11.7 | 19.6 | 0.19 | p-values are not from formal hypothesis testing and are displayed for descriptive purposes only

FIG. 7

Pre-procedure Lesion Analysis I

|  | Diabetics $N_L = 61$ | Non-Diabetics $N_L = 254$ | p value |
|---|---|---|---|
| Lesion Characteristics (%) | | | |
| Angulation (≥ 45°) | 4.9 | 4.0 | 0.72 |
| Calcification (Moderate/Severe) | 11.5 | 13.5 | 0.83 |
| Eccentric | 93.4 | 97.6 | 0.11 |
| Thrombus | 0.0 | 2.0 | 0.59 |
| TIMI 0 | 0.0 | 0.4 | 1.00 |
| ACC/AHA Lesion Type B2 and C (%) | 42.6 | 40.0 | TBC |
| Lesion Length | | | |
| Mean (mm) | 11.3 | 10.9 | 0.46 |
| >20 mm (%) | 1.6 | 4.0 | 0.70 | p-values are not from formal hypothesis testing and are displayed for descriptive purposes only

FIG. 8

Pre-procedure Lesion Analysis II

|  | Diabetic $N_L = 61$ | Non Diabetic $N_L = 254$ | p value |
|---|---|---|---|
| Percent Diameter Stenosis (%) | 60.7 ± 9.9 | 59.3 ± 10.0 | 0.33 |
| Reference Vessel Diameter (mm) | 2.6 ± 0.3 | 2.6 ± 0.4 | 0.51 |
| Minimal Lumen Diameter (mm) | 1.0 ± 0.3 | 1.0 ± 0.3 | 0.74 | p-values are not from formal hypothesis testing and are displayed for descriptive purposes only

FIG. 9

Vessel Treatment

|  | Diabetics $N_L = 61$ | Non-Diabetics $N_L = 254$ | p value |
|---|---|---|---|
| Target Vessel (%) |  |  |  |
| LAD | 26.2 | 43.7 | 0.01 |
| RCA | 41.0 | 26.8 | 0.04 |
| LCX | 32.8 | 28.7 | 0.54 |
| Ramus | 0 | 1 | 1.00 | p-values are not from formal hypothesis testing and are displayed for descriptive purposes only

FIG. 10

Acute Procedural Outcomes

|  | Diabetics N = 60 | Non-Diabetics N = 241 | p value |
|---|---|---|---|
| Clinical Device Success (per lesion)* (%) | 100 | 98.4 | 1.00 |
| Clinical Procedure Success (per patient)** (%) | 100 | 96.7 | 0.36 |

* Clinical device success is defined as successful delivery and deployment of the ABSORB BVS at the target lesion and successful withdrawal of the scaffold delivery system with attainment of final residual stenosis < 50% by QCA.
** Clinical procedure success is defined as a clinical device success without the occurrence of ischemia driven major adverse cardiac event (MACE) during the hospital stay with a maximum of first seven days post index procedure.

p-values are not from formal hypothesis testing and are displayed for descriptive purposes only

FIG. 11

Post-procedure QCA Analysis

|  | Diabetic $N_L$ = 61 | Non-Diabetic $N_L$ = 254 | p value |
|---|---|---|---|
| Percent Diameter Stenosis (%) | | | |
| In-Segment | 19.7 ± 6.3 | 21.0 ± 7.3 | 0.16 |
| In-Scaffold | 16.1 ± 6.0 | 15.4 ± 5.9 | 0.43 |
| Minimal Lumen Diameter (mm) | | | |
| In-Segment | 2.1 ± 0.3 | 2.1 ± 0.3 | 0.27 |
| In-Scaffold | 2.3 ± 0.3 | 2.2 ± 0.3 | 0.66 |
| Acute Gain (mm) | | | |
| In-Segment | 1.1 ± 0.3 | 1.0 ± 0.3 | 0.17 |
| In-Scaffold | 1.2 ± 0.3 | 1.2 ± 0.3 | 0.49 | p-values are not from formal hypothesis testing and are displayed for descriptive purposes only

FIG. 12

Clinical Results Through 180 Days

|  | Diabetic N = 60 | Non-Diabetic N = 241 | p value |
|---|---|---|---|
| MACE* (%) | 0.0 (0) | 4.1 (10) | 0.22 |
| TVF** (%) | 0.0 (0) | 4.6 (11) | 0.13 |
| Non-Hierarchical | | | |
| Cardiac Death (%) | 0.0 (0) | 0.4 (1) | 1.00 |
| Myocardial Infarction (%) | 0.0 (0) | 2.9 (7) | 0.35 |
| Q-Wave MI (%) | 0.0 (0) | 0.8 (2) | 1.00 |
| Non-Q Wave MI (%) | 0.0 (0) | 2.1 (5) | 0.59 |
| Target Vessel Myocardial Infarction (%) | 0.0 (0) | 2.9 (7) | 0.35 |
| Q-Wave TVMI (%) | 0.0 (0) | 0.8 (2) | 1.00 |
| Non-Q Wave TVMI (%) | 0.0 (0) | 2.1 (5) | 0.59 |
| ID-TLR (%) | 0.0 (0) | 1.2 (3) | 1.00 |
| ID-TVR including TLR (%) | 0.0 (0) | 1.7 (4) | 0.59 |

* Cardiac Death, Protocol Myocardial Infarction (MI) and Ischemic Driven Target Lesion Revascularization (ID-TLR)
** Cardiac Death, Protocol MI, ID-TLR, ID-Target Vessel Revascularization

FIG. 13

Scaffold Thrombosis Through 194 Days
(ARC Defined Def/Probable)

|  | Diabetics | Non-Diabetics | p value |
|---|---|---|---|
| <1 day (Acute) (%) | 0.0 (0/60) | 0.0 (0/241) | NA |
| 1 – 30 days (Subacute) (%) | 0.0 (0/60) | 0.4 (1/241) | 1.00 |
| 31 – 194 days (Late) (%) | 0.0 (0/60) | 0.0 (0/240) | NA |
| Cumulative to 194 days (%) | 0.0 (0/60) | 0.4 (1/240) | 1.00 |

97% of patients on Clopidogrel, Ticlopidine or Prasugrel at 180 days (both cohorts)

p-values are not from formal hypothesis testing and are displayed for descriptive purposes only Demographics of Patients at 12 months

|  | Diabetics (N = 62) | Non-Diabetics (N = 188) |
|---|---|---|
| Male (%) | 79.0 | 72.9 |
| Mean Age (years) | 61.2 | 62.4 |
| Prior Cardiac Intervention on Target Vessel (%) | 8.1 | 4.8 |
| Previous MI (%) | 27.4 | 29.9 |
| Unstable Angina (%) | 40.3 | 33.5 |
| Dyslipidemia req. Med. (%) | 58.1 | 60.1 |
| Hypertension req. Med. (%) | 72.6 | 60.6 |
| Current Smoker (%) | 17.7 | 20.7 |

FIG. 16

Lesion Characteristics

|  | Diabetics (L = 64)[1] | Non-Diabetics (L = 201) |
|---|---|---|
| Lesion Characteristics (%) | | |
| Angulation (≥ 45°) | 3.2 | 4.5 |
| Calcification (Moderate/Severe) | 10.9 | 12.4 |
| Eccentric | 92.1 | 97.0 |
| Thrombus | 0.0 | 1.0 |
| ACC/AHA Lesion Classification (%) | | |
| A | 3.2 | 3.0 |
| B1 | 58.7 | 56.3 |
| B2 | 36.5 | 33.7 |
| C | 1.6 | 7.0 |

[1] Note: L is the number of target lesions

FIG. 17

Clinical Outcome at 12 Months

| Non-Hierarchical | Diabetics (N=62) | Non-Diabetics (N=188) |
|---|---|---|
| Cardiac Death % (n) | 0.0 (0) | 0.5 (1) |
| Myocardial Infarction (per protocol) % (n) | 1.6 (1) | 3.2 (6) |
| Q-wave MI | 0.0 (0) | 1.6 (3) |
| Non Q-wave MI | 1.6 (1) | 1.6 (3) |
| Ischemia driven TLR % (n) | 1.6 (1) | 2.1 (4) |
| CABG | 0.0 (0) | 0.0 (0) |
| PCI | 1.6 (1) | 2.1 (4) |
| Ischemia driven non-TL TVR % (n) | 0.0 (0) | 1.1 (2) |
| CABG | 0.0 (0) | 0.5 (1) |
| PCI | 0.0 (0) | 0.5 (1) |
| Hierarchical MACE % (n) | 3.2 (2) | 4.8 (9) |
| Hierarchical TVF % (n) | 3.2 (2) | 5.3 (10) |
| Hierarchical TLF % (n) | 3.2 (2) | 4.8 (9) |
| Scaffold Thrombosis (def/prob) % (n) | 0.0 (0) | 1.1 (2) |

FIG. 18

BIORESORBABLE POLYMER SCAFFOLD TREATMENT OF CORONARY AND PERIPHERAL ARTERY DISEASE IN DIABETIC PATIENTS

CROSS-REFERENCE TO RELATED APPLICATION

This application claims the benefit of U.S. patent application Ser. No. 61/607,977, filed on Mar. 7, 2012, which is incorporated by reference in its entirety, including any drawings, and for all purposes, herein.

BACKGROUND OF THE INVENTION

Field of the Invention

This invention relates to methods of treatment of coronary and peripheral artery disease of diabetic patients with bioresorbable polymer scaffolds.

Description of the State of the Art

This invention relates generally to methods of treatment with radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must have sufficient radial strength so that it is capable of withstanding the structural loads, namely radial compressive forces imposed on the stent as it supports the walls of a vessel. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents made from biostable or non-degradable materials, such as metals that do not corrode or have minimal corrosion during a patient's lifetime, have become the standard of care for percutaneous coronary intervention (PCI) as well as in peripheral applications, such as the superficial femoral artery (SFA). Such stents have been shown to be capable of preventing early and later recoil and restenosis.

In order to effect healing of a diseased blood vessel, the presence of the stent is necessary only for a limited period of time, as the artery undergoes physiological remodeling over time after deployment. The development of a bioabsorbable stent or scaffold could obviate the permanent metal implant in the vessel, allow late expansive luminal and vessel remodeling, and leave only healed native vessel tissue after the full resorption of the scaffold. Stents fabricated from bioresorbable, biodegradable, bioabsorbable, and/or bioerodable materials such as bioabsorbable polymers can be designed to completely absorb only after or some time after the clinical need for them has ended. Consequently, a fully bioabsorbable stent can reduce or eliminate the risk of potential long-term complications and of late thrombosis, facilitate non-invasive diagnostic MRI/CT imaging, allow restoration of normal vasomotion, and provide the potential for plaque regression.

Differences in the treatment results of percutaneous coronary intervention for diabetic and non-diabetic patients have been observed when using non-biodegradable stents. The clinical outcomes for diabetic patients have generally been less favorable than for non-diabetic patients. For example, one study found that after a percutaneous cardiac intervention followed by the implantation of a bare metal stent (no coating), the rate of restenosis was 30% for diabetic patients compared to 20% for non-diabetic patients. Early studies with drug eluting stents (DES) showed higher rates of restenosis for diabetic patients as compared to non-diabetic patients. As an example, a study involving implantation of a DES, found a rate of 14.6% restenosis in non-diabetics, but 20.9% for diabetic patients. In general, diabetics are more than twice as likely as non-diabetics to have a heart attack or stroke, and 2 out of 3 diabetics die from cardiovascular disease. Hyperglycemia, independent of whether or not a person has been diagnosed with diabetes, is a risk-factor for cardiovascular events. Thus, there is a need for improved methods for treating vascular diseases and disorders, more particularly in diabetic patients.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if each said individual publication, patent, or patent application was fully set forth, including any figures, herein.

SUMMARY OF THE INVENTION

Various embodiments of the present invention include a method of treating coronary heart disease, peripheral vascular disease, or both, in a patient with diabetes mellitus comprising: deploying a bioabsorbable polymer scaffold at a segment of a coronary artery of a diabetic patient; allowing the deployed bioabsorbable scaffold to provide support to the segment; and allowing the deployed scaffold to resorb from the segment.

Further embodiments of the present invention include a method of treating coronary heart disease in a patient with diabetic mellitus comprising: deploying a bioresorbable polymer scaffold in a coronary artery of a diabetic patient, wherein the scaffold comprises a target dose per unit scaffold length of an antiproliferative drug of 8 to 13 µg/mm; wherein a thickness of struts of the scaffold is greater than 150 microns, and wherein a compliance of the scaffold increases with time after deployment, eventually allowing restoration of natural vasomotion to the artery. In some embodiments, the drug is everolimus.

BRIEF DESCRIPTION OF THE DRAWINGS

FIG. 5 depicts the total platelet LDH and the mean platelet LDH per surface area for the BMS Multi-Link Vision stent, Xience V stent, and the BVS scaffold.

FIG. 6 provides the diabetes incidence/status of the patients in the EXTEND clinical trial at the 180 day time point.

FIG. 7 provides the baseline demographics of the diabetic and non-diabetic patients in the EXTEND clinical trial at the 180 day time point.

FIG. 8 provides the pre-procedural lesion analysis I of the diabetic and non-diabetic patients in the EXTEND clinical trial at the 180 day time point.

FIG. 9 provides the pre-procedural lesion analysis II in the EXTEND clinical trial at the 180 day time point.

FIG. 10 provides vessel treatment data for diabetic and non-diabetic patients in the EXTEND clinical trial at the 180 day time point.

FIG. 11 provides acute procedural outcomes for diabetic and non-diabetic patients in the EXTEND clinical trial at the 180 day time point.

FIG. 12 provides the post-procedural QCA analysis for diabetic and non-diabetic patients in the EXTEND clinical trial at the 180 day time point.

FIG. 13 provides the clinical results through 180 days for diabetic and non-diabetic patients in the EXTEND clinical trial.

FIG. 16 provides the baseline demographics of the diabetic and non-diabetic patients in the EXTEND clinical trial at the 12 month time point.

FIG. 17 provides the pre-procedural lesion analysis II in the EXTEND clinical trial at the 12 month time point.

FIG. 18 provides the clinical results through 12 months for diabetic and non-diabetic patients in the EXTEND clinical trial.

DETAILED DESCRIPTION OF THE INVENTION

Figure 1:
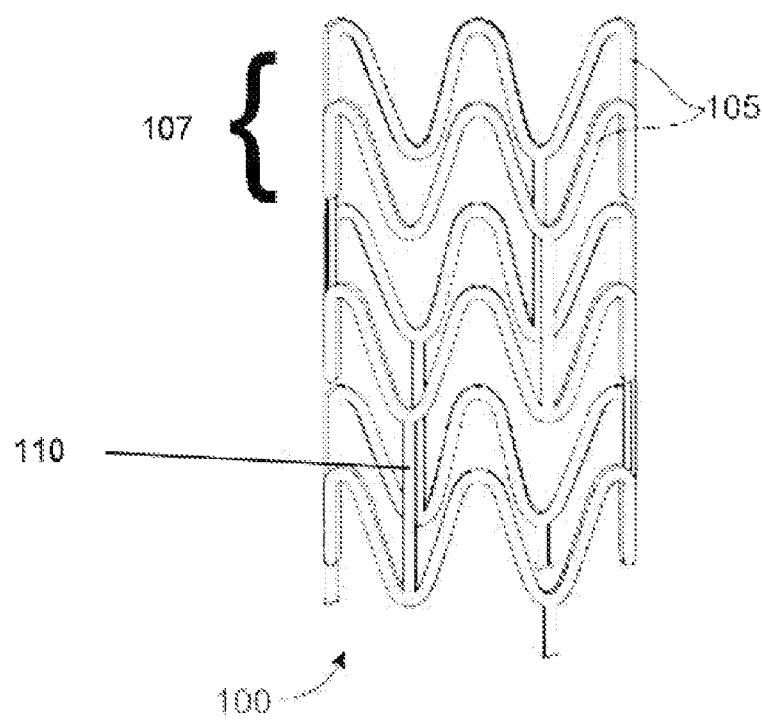
FIG. 1 depicts an exemplary stent scaffold.

Various embodiments of the present invention include treatment of coronary artery disease and peripheral artery disease in diabetic patients with bioresorbable polymer stents. These methods of treatment generally result in lower rates of adverse events and failure than prior art methods. The bioresorbable stents can include a support structure in the form of a scaffold made of a material that is bioresorbable, for example, a bioresorbable polymer such as a lactide-based polymer. The scaffold is designed to completely erode away from an implant site after treatment of an artery is completed. The scaffold can further include a drug, such as an antiproliferative or an anti-inflammatory agent. A polymer coating disposed over the scaffold can include the drug which is released from the coating after implantation of the stent. The polymer of the coating is also bioresorbable.

The present invention is applicable to, but is not limited to, self-expandable stents, balloon-expandable stents, stent-grafts, and generally tubular medical devices in the treatment of artery disease. The present invention is further applicable to various stent designs including wire structures, and woven mesh structures.

Self-expandable or self-expanding stents include a bioabsorbable polymer scaffold that expands to the target diameter upon removal of an external constraint. The self-expanding scaffold returns to a baseline configuration (diameter) when an external constraint is removed. This external constraint could be applied with a sheath that is oriented over a compressed scaffold. The sheath is applied to the scaffold after the scaffold has been compressed by a crimping process. After the stent is positioned at the implant site, the sheath may be retracted by a mechanism that is available at the end of the catheter system and is operable by the physician. The self-expanding bioabsorbable scaffold property is achieved by imposing only elastic deformation to the scaffold during the manufacturing step that compresses the scaffold into the sheath.

The bioabsorbable scaffold may also be expanded by a balloon. In this embodiment the scaffold is plastically deformed during the manufacturing process to tightly compress the scaffold onto a balloon on a catheter system. The scaffold is deployed at the treatment site by inflation of the balloon. The balloon will induce areas of plastic stress in the bioabsorbable material to cause the scaffold to achieve and maintain the appropriate diameter on deployment.

A stent scaffold can include a plurality of cylindrical rings connected or coupled with linking elements. For example, the rings may have an undulating sinusoidal structure. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are generally non-load bearing, serving to maintain connectivity between the rings. For example, a stent may include a scaffold composed of a pattern or network of interconnecting structural elements or struts.

FIG. 1 depicts a view of an exemplary stent 100. In some embodiments, a stent may include a body, backbone, or scaffold having a pattern or network of interconnecting structural elements 105. Stent 100 may be formed from a tube (not shown). FIG. 1 illustrates features that are typical to many stent patterns including undulating sinusoidal cylindrical rings 107 connected by linking elements 110. As mentioned above, the cylindrical rings are load bearing in that they provide radially directed force to support the walls of a vessel. The linking elements generally function to hold the cylindrical rings together. A structure such as stent 100 having a plurality of structural elements may be referred to as a stent scaffold or scaffold. Although the scaffold may further include a coating, it is the scaffold structure that is the load bearing structure that is responsible for supporting lumen walls once the scaffold is expanded in a lumen.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped on to a balloon or catheter for delivery into a bodily lumen. Alternatively, the scaffold design may be composed of radial bands that slide to increase the diameter of the scaffold. Such a design utilizes a locking mechanism to fix the stent at a target diameter and to achieve final radial strength. In other embodiments, the scaffold design could be braided polymer filaments or fibers.

Diabetic patients refer to human patients having the condition diabetes mellitus, often simply referred to as diabetes, which is a group of metabolic diseases in which a person has high blood sugar, either because the body does not produce enough insulin, or because cells do not respond to the insulin that is produced. This high blood sugar can produce the symptoms of polyuria (frequent urination), polydipsia (increased thirst) and polyphagia (increased hunger).

There are three main types of diabetes. The first, Type 1 diabetes, results from the body's failure to produce insulin, and presently requires the person to inject insulin. Type 1 diabetes is also referred to as insulin-dependent diabetes mellitus, IDDM for short, and juvenile diabetes.

The second, type 2 diabetes, results from insulin resistance, a condition in which cells fail to use insulin properly, sometimes combined with an absolute insulin deficiency. Type 2 diabetes is formerly referred to as non-insulin-dependent diabetes mellitus, NIDDM for short, and adult-onset diabetes.

The third, gestational diabetes is when pregnant women, who have never had diabetes before, have a high blood glucose level during pregnancy. It may precede development of type 2 diabetes.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes. Differences in the treatment results of percutaneous coronary intervention for diabetic and non-diabetic patients have been observed when using non-biodegradable stents. The clinical outcomes for diabetic patients have generally been less favorable than for non-diabetic patients. The disease characteristics of diabetes tend to present challenges in such treatment.

In particular, patients with diabetes mellitus undergoing percutaneous coronary intervention with bare metal stents have higher rates of angiographic and clinical restenosis than patients without diabetes mellitus. A bare metal stent refers to a stent including a metal support structure (e.g., scaffold) made of a metal that is not degradable and that has no coating, such as a polymer coating, on its surface. Exemplary bare metal stents can be made of stainless steel, nickel titanium alloy (NiTi), and cobalt chromium alloy.

Compared with bare metal stents, drug-eluting stents (DES) that are not bioresorbable have been shown to be safe and to result in greater absolute reductions in target lesion revascularization (TLR) and target vessel revascularization in diabetic patients versus non-diabetic patients. A DES refers to a stent including a support structure (e.g., scaffold) and also includes a drug eluting coating over the support structure. The coating can include a polymer and a drug. The polymer functions as a drug reservoir for delivery of the drug to a vessel. The polymer can be non-biodegradable or bioresorbable. The DES that are not bioresorbable include a metal support structure with a drug eluting coating.

However, whether the presence of diabetes mellitus differentially affects the relative clinical outcomes with different types of DES is a matter of considerable debate. Different types of DES refer to DES stents that differ in the polymer of the coating, the type of drug in the coating, or both. Most studies have shown comparable rates of angiographic in-stent late loss and clinical restenosis with paclitaxel-eluting stents (PES) in patients with versus patients without diabetes mellitus.

In contrast, whether the relatively greater suppression of neointimal hyperplasia observed from stents that elute everolimus (EES) over PES is preserved in patients with diabetes mellitus is unsettled. In this regard, several small to moderate sized studies have provided conflicting results. Moreover, none of these prior trials was powered to determine whether there are differences in safety outcomes between different DES according to the presence of diabetes mellitus.

Several clinical trials involving different types of DES stents have provided insight into the safety and efficacy of such stents for diabetic patients. Specifically, the Spirit II, III, and IV trials involve evaluation of the safety and efficacy of the XIENCE V® Everolimus Eluting Coronary Stent System. In these trials, the XIENCE V® system is compared to an active control, represented by the FDA-approved TAXUS® EXPRESS2™ Paclitaxel-Eluting Coronary Stent System (TAXUS®), commercially available from Boston Scientific (clinical.trial.gov).

Figure 2:
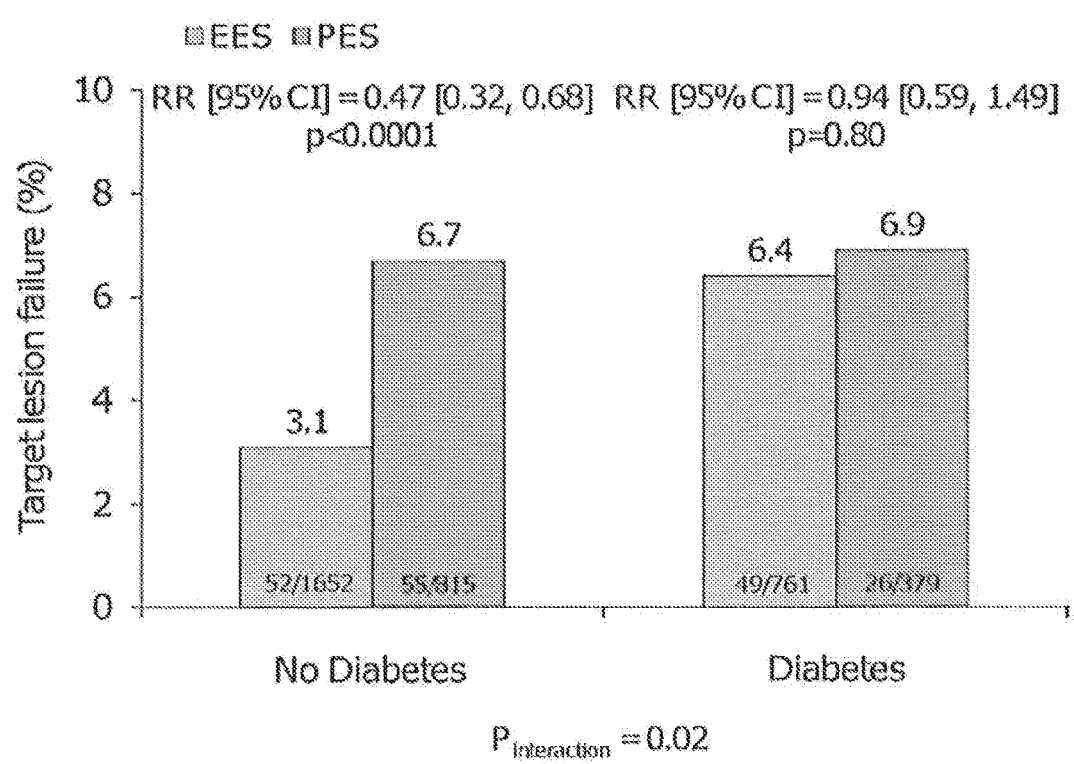
FIG. 2 shows clinical results from the SPIRIT IV trials.

FIG. 2 shows clinical results from the SPIRIT IV trial. In the SPIRIT IV trial, the diabetic cohort analysis showed: 1) even though EES compared with PES markedly reduced adverse clinical outcomes at 1 year in nondiabetic patients, results in diabetic patients were comparable, regardless of stent type; and 2) no differences in 1-year clinical outcomes after EES versus PES were observed in patients with diabetes, regardless of insulin requirement.

The SPIRIT IV trial confirmed and extended the observation made earlier in the SPIRIT III trial of a significant interaction between randomized stent type (EES vs. PES) and the presence of diabetes on the primary composite clinical end point. However, explanation(s) for the apparent attenuation in the relative benefit afforded by EES versus PES among diabetic patients is unknown.

Figure 3:
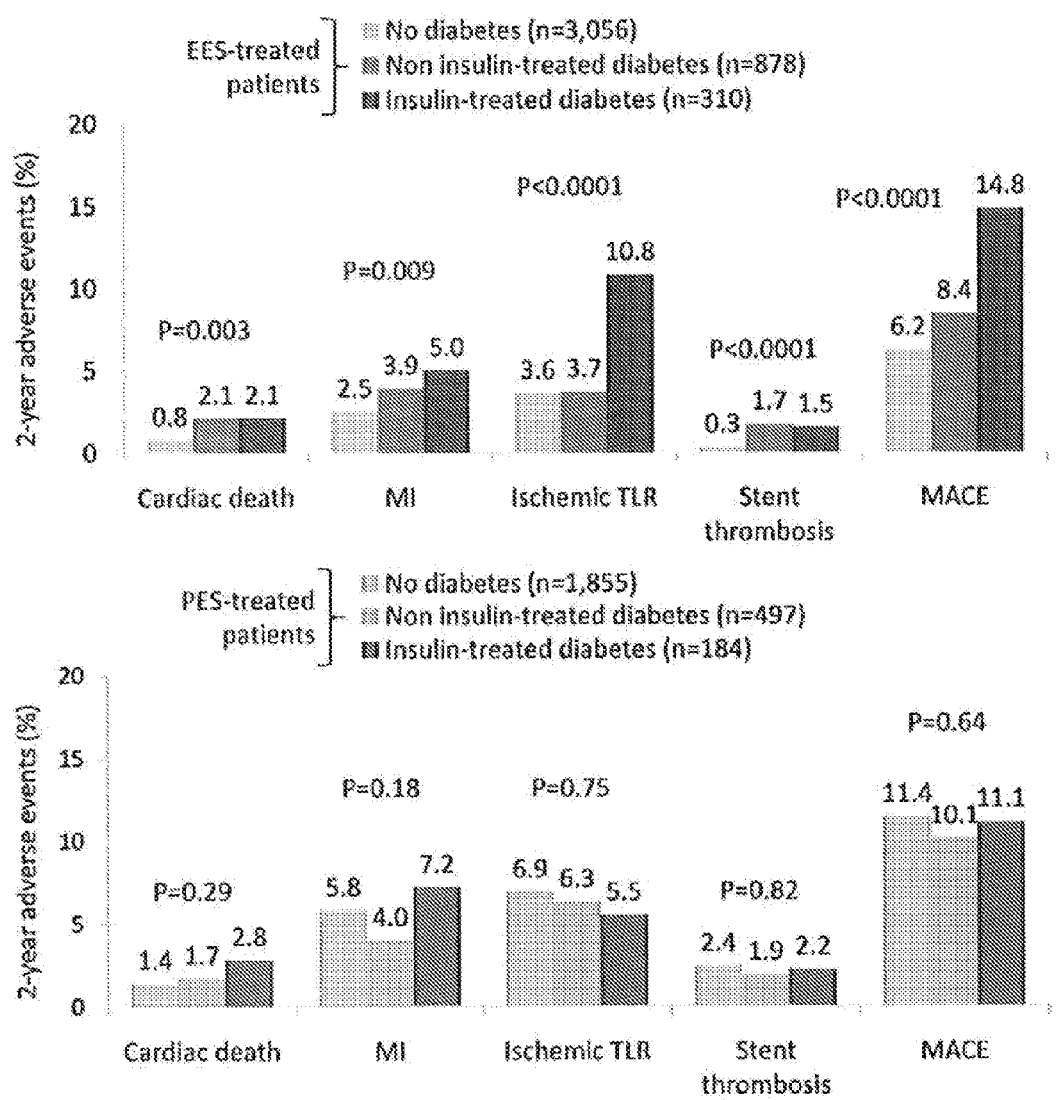
FIG. 3 depicts clinical results from the SPIRIT II, III, IV, and COMPARE trials.

FIG. 3 depicts clinical results from the SPIRIT II, III, IV, and COMPARE trials. In the COMPARE trial, the main objective is a head to head comparison of the everolimus coated XIENCE-V™ stent with the paclitaxel coated TAXUS™ stent in order to observe whether there is a difference in clinical outcome between both stents (clinicaltrials.gov). In a pooled analysis of these four randomized controlled trials (SPIRIT II, III, IV and COMPARE), the largest study to date evaluating the relative safety and efficacy of different DES types stratified by the presence of diabetes mellitus, it was demonstrated:

(1) that a significant interaction was present between diabetic status and treatment with EES compared with PES on the relative risk of 2-year clinical outcomes, reflecting measures of both safety and efficacy;

(2) that in patients without diabetes mellitus, treatment with EES compared with PES reduced the 2 year rates of death, myocardial infarction (MI), stent thrombosis, ischemia-driven TLR, and (major adverse cardiac events) MACE, whereas in patients with diabetes mellitus, there were no significant differences in clinical outcomes at 2 years between the stent types; and (3) that an additional interaction was identified among patients with diabetes mellitus so that the 2-year rate of ischemia-driven TLR was reduced with EES compared with PES in those not requiring insulin, whereas the opposite trend was observed in those who were treated with insulin.

Based on the results of these and other clinical trials, there is currently an unmet clinical need for a drug eluting stent for treatment of diabetic patients that yields lower clinical event rates than existing drug eluting stents.

The ABSORB Bioresorbable everolimus eluting vascular scaffold (ABSORB BVS) of Abbott Vascular Inc. of Santa Clara, Calif. was recently developed to provide an approach to treating coronary artery lesions with transient vessel support and drug delivery. Preclinical evaluation in an animal model demonstrated substantial polymer degradation at 2-years post ABSORB BVS implantation, with complete disappearance of the BVS strut "footprint" in the vessel wall within a 3-4 year period. The first generation BVS (BVS revision 1.0) was tested in the ABSORB cohort A trial and demonstrated promising results with a low event clinical rate at up to 4 years follow up (EuroIntervention 2012; 7:1060-1061). The device was however limited by a slightly higher acute recoil compared to conventional metallic platform stents.

Improvements in design were therefore introduced in the second generation BVS (BVS revision 1.1), notably an enhanced mechanical strength, more durable support to the vessel wall, a reduced maximum circular unsupported surface area and a more uniform strut distribution and drug delivery. The performance of the next generation BVS revision 1.1 was subsequently investigated in the ABSORB Cohort B Trial which reported excellent clinical results at 1 and 2 year follow-up (J Am Coll Cardiol. 2011; 58: B66).

Figure 4A:
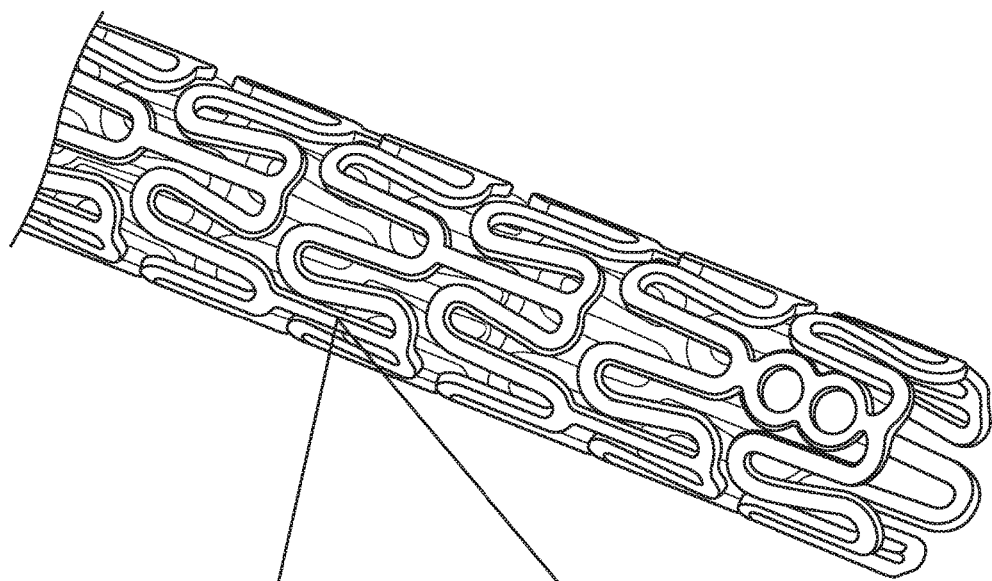
FIGS. 4A-B depict the Abbott Vascular Inc. BVS revision 1.1 scaffold.
Figure 4B:
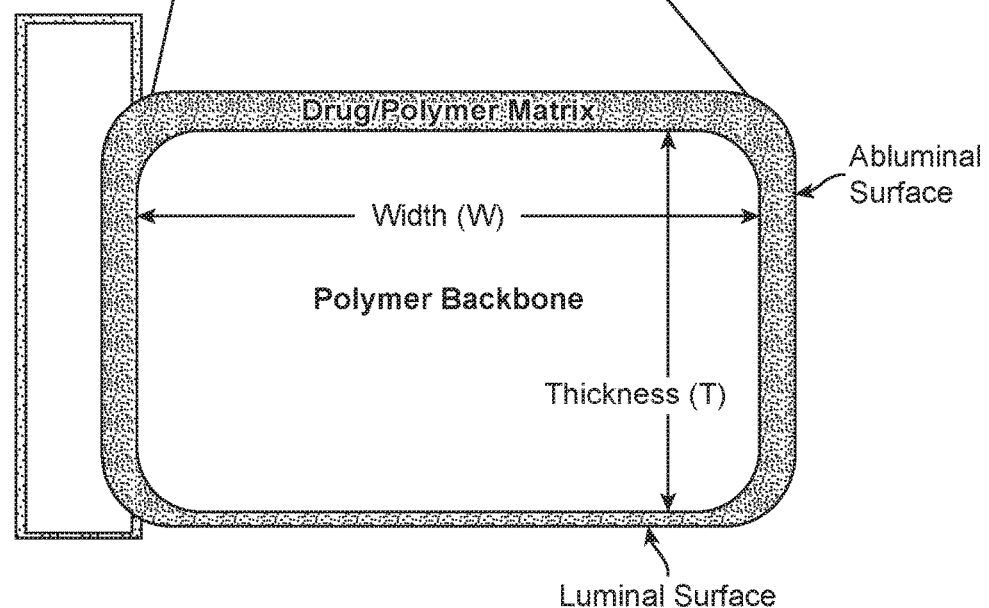

FIGS. 4A-B depict the BVS revision 1.1 scaffold. FIG. 4A shows the scaffold in a crimped configuration. FIG. 4B show a cross-selection of a strut showing the polymer backbone or core of the strut surrounded by a drug/polymer matrix. The cross-section of the strut has an abluminal surface or side that faces the vessel wall and a luminal surface or side that faces the lumen of the vessel. The strut cross-section shown is rectangular with rounded corners with a width (W) and thickness T. The BVS revision 1.1 scaffold is approximately square with an aspect ratio T/W close to 1.

The polymer backbone is made of poly(L-lactide). The diameter of the scaffold is 3 mm and the length is 18 mm. The struts have a width of about 165 microns and thickness of about 152 microns. The coating is a mixture of poly(DL-lactide) and everolimus with a 1:1 (weight:weight) ratio of polymer to drug. The coating is about 2 to 2.5 microns in thickness. The drug dose density is 100 $\mu g/cm^2$, which is the drug mass per scaffold surface area. The surface area of the scaffold is 160 $mm^2$, so the target drug dose is about 160 $\mu g$. The surface area of the scaffold per unit scaffold length is about 8.9 $mm^2/mm$.

In general, the treatment with bioabsorbable polymer stents has a number of advantages over permanent implants: (i) The stent disappears from the treated site resulting in reduction or elimination of late stent thrombosis; (ii) disappearance of the stent facilitates repeat treatments (surgical or percutaneous) to the same site; (iii) disappearance of the stent allows restoration of vasomotion at the treatment site (the presence of a rigid permanent metal stent restricts vasomotion); (iv) the bioabsorbability results in freedom from side-branch obstruction by struts; and (v) the disappearance results in freedom from strut fracture and ensuing restenosis. Some of these advantages may be relevant to improving clinical outcomes for diabetic patients.

In the short term and over the long term, a bioresorbable scaffold has the advantage of being less traumatic to the vessel wall. The vasculature of diabetic patients tends to be more susceptible to trauma. Since the bioresorbable scaffold degrades with time and eventually disappears, trauma associated with the presence of a scaffold decreases with time and eventually disappears.

The vascular intervention in a diabetic patient has also been shown to have an elevated thrombotic risk. As indicated above, resorption of a bioresorbable scaffold restores vasomotion of the vessel wall.

Additionally, there is evidence that a polymer-based scaffold itself may be less thrombogenic. The thrombogenic potential has been evaluated based on platelet adhesion to the BVS cohort B scaffold deployed ex vivo. Platelets are indispensable initiators of thrombosis and their adhesion to intravascular devices is the critical step in the thrombus formation. In a study of platelet adhesion, metallic coronary stents (BMS Multilink Vision™ and XIENCE V®) and BVS scaffolds were deployed in a Chandler Loop perfused with freshly prepare porcine platelet rich plasma (PRP) instead of whole blood.

The extent of platelet adhesion is determined by measuring the LDH activity extracted from the adherent platelets which is directly proportional to the number of platelets. Such properties may be of particular benefit in diabetic vascular disease.

FIG. 5 depicts the total platelet LDH and the mean platelet LDH per surface area for the BMS Multi-Link Vision and Xience V stents and BVS scaffolds. Thrombogenicity based on the adhesion of platelets was consistently the highest for the BMS Multi-Link Vision followed by the Xience V stents and followed by the BVS scaffolds.

Additionally, the hyperglycemic milieu in diabetic patients results in a heightened proliferative vascular response after stenting. Hyperglycemia or high blood sugar, is a condition in which an excessive amount of glucose circulates in the blood plasma, resulting in a higher viscosity of the plasma. Thicker scaffold struts with a higher total dose of drug may be beneficial in diabetic vascular disease, where neointimal hyperplasia is exaggerated, as a result of increased smooth muscle cell proliferation. The thicker struts in the BVS scaffold, about 150 to 165 microns, results in a total dose of everolimus that is almost two fold higher than XIENCE V.

The EXTEND Cohort B trial has been initiated to further examine performance and clinical outcomes of the BVS ABSORB. EXTEND is the first BVS trial that includes diabetic patients. At the 180 day time point, the EXTEND trial had recruited 241 non-diabetic patients and 60 diabetic patients. The EXTEND trial treatment allows inclusion of up to two de novo lesions in separate epicardial arteries.

Figures 14, 15:
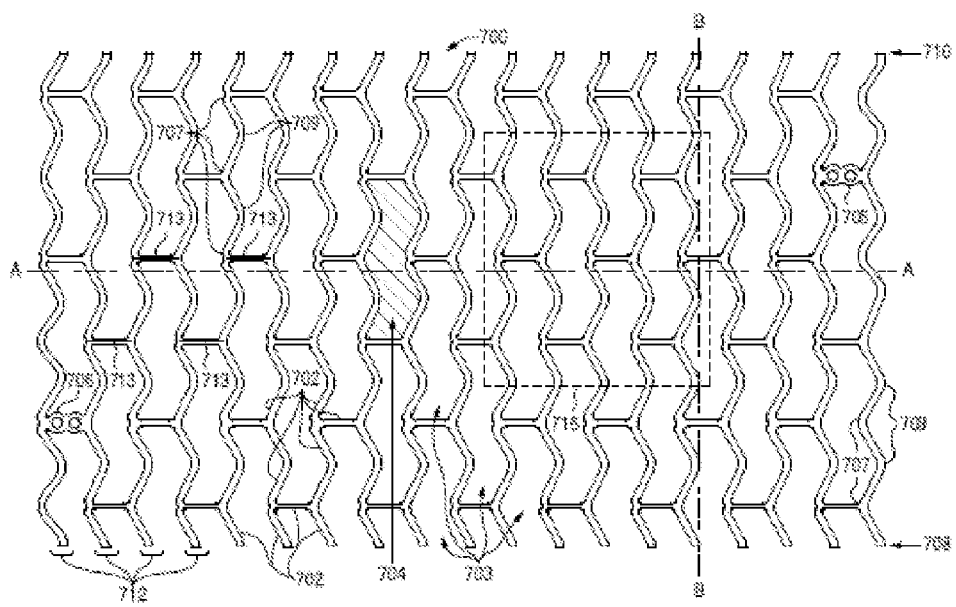
FIG. 14 provides the scaffold thrombosis through 194 days for diabetic and non-diabetic patients in the EXTEND clinical trial.
FIG. 15 depicts an exemplary stent pattern shown in a planar or flattened view.

FIGS. 6-14 provide patient information and results up to 180 days for the EXTEND trial. FIG. 6 provides the diabetes incidence/status of the patients. FIG. 7 provides the baseline demographics of the diabetic and non-diabetic patients. FIG. 8 provides the pre-procedural lesion analysis I of the diabetic and non-diabetic patients. FIG. 9 provides the pre-procedural lesion analysis II. FIG. 10 provides the vessel treatment data for diabetic and non-diabetic patients. FIG. 11 provides the acute procedural outcomes for diabetic and non-diabetic patients. FIG. 12 provides the post-procedural QCA analysis for diabetic and non-diabetic patients. FIG. 13 provides the clinical results through 180 days for diabetic and non-diabetic patients. FIG. 14 provides the scaffold thrombosis through 194 days for diabetic and non-diabetic patients.

Preliminary data in these first 60 diabetic patients treated in the EXTEND trial for 180 days have demonstrated extremely good clinical outcomes. FIG. 13 shows that no adverse events were reported for diabetic patients at 180 days, and that the MACE rates between diabetic and non-diabetic patients are comparable. FIG. 14 shows no scaffold thrombosis through 194 days.

FIGS. 16-18 provide patient information and results observed at 12 months for the EXTEND trial. FIG. 16 provides the baseline demographics for the 250 patients for which data is available at the 12 month time point (database lock of 18 Sep. 2012). FIG. 17 provides lesion characteristics. Clinical outcome at 12 months is presented in FIG. 18. As shown in FIG. 18, there is no scaffold thrombosis in diabetic patients, and 1.1% thrombosis in non-diabetic patients. The incidence for MACE, TVF, and TLF is about equal or tending to slightly lower in diabetic patients as compared to non-diabetic patients. The higher drug concentration and intrinsic properties of the bioresorbable scaffold may thus be an ideal therapy for diabetic vascular disease.

In summary, from the SPIRIT IV trial, for an everolimus eluting nonresorbable stent, the target lesion failure at 12 months was 3.1% for non-diabetic patients and 6.4% for diabetic patients. In contrast, the 12 month time point in the EXTEND trial using a bioabsorbable everolimus eluting stent exhibits target lesion failure rates of 2.1% for non-diabetic patients and 1.6% for diabetic patients.

For a nonresorbable stent which elutes everolimus, the rate of cardiac death at 2 years was 0.8, while it was 2.1 and 2.1 for non-insulin treated diabetic patients and insulin treated diabetic patients, respectively. In contrast, for the absorbable stent, the rate of cardiac death at 12 months was 0.5% for non-diabetic patients, and 0% for diabetic patients. With respect to MACE, a nonabsorbable stent which elutes everolimus, the rate of MACE was 6.2% for non-diabetic patients, while it was 8.4% and 14.8% for non-insulin treated diabetic patients and insulin treated diabetic patients, respectively. In contrast, for the absorbable stent, the rate of MACE at 12 months was 4.8% for non-diabetic patients, and 3.2% for diabetic patients. Thus, it appears that the clinical outcomes are generally less good for diabetic patients as compared to non-diabetic patients for an everolimus eluting non-resorbable stent with a metal scaffold, while the clinical outcomes are about the same, or tending to slightly lower, for diabetic patients as compared to non-diabetic patients for an everolimus eluting bioabsorbable stent with a polymeric scaffold.

It is believed that favorable clinical outcomes thus far for diabetic patients may be due to one or more aspects of the bioresorbable scaffold. Favorable outcomes may also be due to the synergy provided by combinations of two or more of these aspects.

One aspect is the use of a polymer, in particular a bioresorbable polymer, for the scaffold. A polymer scaffold may be less traumatic to a vasculature. Polymers are softer, less stiff or have a lower modulus than metals. Thus, the presence of a softer, more flexible implant may be less traumatic to a soft, flexible vessel segment than a metal implant. For example, aliphatic bioresorbable polymers have tensile moduli generally less than 7 GPa and in the range of 2 to 7 GPa (US2009/0182415). Poly(L-lactide) has a tensile modulus of about 3 GPa.

Metals used to make stents and their approximate moduli include stainless steel 316L (143 GPa), tantalum (186), Nitinol or nickel-titanium alloy (83 GPa), and cobalt chromium alloys (243 GPa). These moduli are significantly higher than aliphatic polymers. The strengths of these metals are also significantly higher than the polymers as well. As a result, a bioresorbable polymeric scaffold has thicker struts to compensate for the difference in the material properties to provide a radial stiffness and radial strength that is sufficient to provide patency.

Also, the mismatch of the properties of a polymer scaffold and a vessel segment is lower than for a metallic scaffold. This mismatch can be expressed formally in terms of compliance mismatch between the scaffold and the vessel segment at the implant site. The compliance of a material, which is the inverse of stiffness or modulus of a material, refers to the strain of an elastic body expressed as a function of the force producing the strain. The compliance of a scaffold or radial compliance of the scaffold can likewise be defined as the inverse of the radial stiffness of the scaffold. The radial stiffness of the bioresorbable scaffold is lower than a metallic scaffold, so the radial compliance of the bioresorbable scaffold is higher than a metallic scaffold. The compliance mismatch of a polymer scaffold is lower than a metallic stent.

The compliance of a stent, both nondegradable and resorbable, is necessarily much lower than the vessel segment in order for the scaffold to support the vessel at a deployed diameter with minimal periodic recoil due to inward radial forces from the vessel walls. Additionally, it results in better conformity (and less straightening) of the scaffold segment to the overall curvature of the adjacent segments in the treated vessel. However, an additional aspect of a bioresorbable polymer scaffold that may contribute to favorable clinical outcomes is that the compliance mismatch decreases with time due to the degradation of the bioresorbable polymer. As the polymer of the scaffold degrades, mechanical properties of the polymer, such as strength and stiffness, decrease, and compliance increases. As a result, the radial strength of the scaffold decreases with time and the compliance of the scaffold increases with time since these properties depend on the properties of the scaffold material.

In the long term, the compliance of a vessel segment with an implanted scaffold converges to that of the natural compliance of the vessel. The convergence of the compliance occurs gradually as the vessel segment heals. Since natural compliance of a vessel segment is eventually restored due to complete resorption of the scaffold, natural vasomotion of the vessel segment is also restored. Compliance mismatch in the treatment with metallic stents is permanent and has been identified as a contributor to the process of restenosis and potentially late adverse events.

Another aspect that may contribute to favorable clinical outcomes of bioresorbable scaffolds is a higher drug loading or target dose of the bioresorbable scaffold. From above, the BVS scaffold in the EXTEND trial is 18 mm long and has a drug dose density of 100 µg/cm² and a target drug dose of about 160 µg. The target drug dose per unit scaffold length of the EXTEND trial scaffold is about 8.9 µg/mm. The delivery of the target dose to the vessel can occur over a period of about 2 to 3 months after implantation.

The drug dose density of the XIENCE V® stent (http://www.accessdata.fda.gov/cdrh_docs/pdf11/P110019b.pdf) and TAXUS Express® (American Heart Journal Volume 163, Number 2, p. 143-148) are both reported to be 100 µg/cm². However, the BVS target dose and dose per unit length is larger due to the wider and thicker struts compared to these stents: XIENCE V® (91 mm×81 mm) and TAXUS Express® (91 mm×132 mm).

Exemplary ranges of drug dose density for diabetic patients include 70 to 130 µg/cm², 80 to 90 µg/cm², 90 to 120 µg/cm², 95 to 105 µg/cm², and 98 to 102 µg/cm². Exemplary ranges of target drug dose for diabetic patients include 150 to 220 µg, 150 to 160 µg, 155 to 165 µg, and 150 to 170 µg. Exemplary ranges for target drug dose per unit scaffold length include 5 to 15 µg/mm, 7 to 15 µg/mm, 7 to 9 µg/mm, 8 to 15 µg/mm, 8 to 13 µg/mm, 8 to 12 µg/mm, 9 to 12 µg/mm, and 9 to 15 µg/mm.

BMS and metallic DES stents typically have strut widths and thicknesses much less than the BVS stent (Interventional Cardiology, Vol. 6, Issue 2, pp. 143-147). The larger strut width and strut thickness, or equivalently, larger surface area of the BVS scaffold, may also contribute to favorable clinical outcomes of diabetic patients. The larger strut width and strut thickness or surface area of a bioresorbable scaffold contributes by providing a higher target dose due to the higher surface area of contact with the vessel walls.

Exemplary strut width and/or strut thickness of a bioresorbable scaffold may be less than 100 microns, less than 140 microns, greater than 140 microns, greater than 150 microns, or greater than 160 microns. Exemplary ranges of strut width and thickness include 80 to 100 microns, 100 to 120 microns, 120 to 140 microns, 140 to 200 microns, 150 to 170 microns, 155 to 170 microns, 155 to 165 microns, 160 to 170 microns, 160 to 180 microns, and 165 to 175 microns. A scaffold may have any combination of strut width and thickness in the above ranges.

Exemplary scaffold surface areas of an 18 mm bioresorbable scaffold may be 90 to 110 mm², 110 to 120 mm², 120 to 140 mm², 130 to 150 mm², 150 to 170 mm², 170 to 190 mm², 190 to 210 mm², and 160 to 200 mm². Exemplary scaffold surface areas per unit scaffold length may be 5 to 6 mm²/mm, 6 to 7 mm²/mm, 7 to 8 mm²/mm, 5 to 8 mm²/mm, 8 to 9 mm²/mm, 9 to 10 mm²/mm, 10 to 11 mm²/mm, 11 to 12 mm²/mm, 11 to 14 mm²/mm, 7 to 11 mm²/mm, 8 to 12 mm²/mm, and greater than 14 mm²/mm. Another aspect that may contribute to favorable clinical outcomes of bioresorbable scaffolds is that the bioresorbable scaffolds may be deployed at lower pressures than metallic stents. The lower pressure deployment reduces trauma on the vessel wall when the scaffold is deployed. A bioresorbable scaffold and a balloon expandable metallic stent are crimped to a reduced diameter over a deflated noncompliant balloon. When the crimped stent is positioned at an implant site, the stent or scaffold is deployed at the treatment site by inflation of the balloon. The inflation of the balloon expands the stent or scaffold at the implant site. The balloon is then deflated and withdrawn from the patient.

Exemplary inflation pressures for a metallic DES stent are 8 and 9 atm, depending on the diameter of the stent (The XIENCE V® and XIENCE Nano™ Everolimus Eluting Coronary Stent System Instructions for Use, www.abbottvascular.com). The nominal inflation pressure used for deployment of the BVS ABSORB stent is 7 atm. Exemplary deployment pressures of a bioresorbable scaffold such as the BVS scaffold are less than 5 atm, 6 atm, 7 atm, and 8 atm. Exemplary deployment pressures of a bioresorbable scaffold such as the BVS scaffold are 4 to 5, 5 to 6, 6 to 7, and 5 to 7 atm. In some embodiments, the balloon inflation rate is 6 psi/second, about 6 psi/second, or lower than 6 psi/second. In some embodiments, the inflation pressure may not be allowed to be above 7 or 8 atm, or deployment may not be performed above 7 or 8 atm, with diabetic patients. In other embodiments, the deployment may also include inflation pressures in the range 8 to 10 atm, 8 to 16 atm, 12 to 16 atm, or 14 to 16 atm.

In a preferred embodiment a scaffold for coronary applications has the stent pattern described in U.S. application Ser. No. 12/447,758 (US 2010/0004735) to Yang & Jow, et al. Other examples of stent patterns suitable for PLLA (Poly(L-lactide)) are found in US 2008/0275537. FIG. 15 depicts exemplary stent pattern 700 from US 2008/0275537. The stent pattern 700 is shown in a planar or flattened view for ease of illustration and clarity, although the stent pattern 700 on a stent actually extends around the stent so that line A-A is parallel or substantially parallel to the central axis of the stent. The pattern 700 is illustrated with a bottom edge 708 and a top edge 710. On a stent, the bottom edge 708 meets the top edge 710 so that line B—B forms a circle around the stent. In this way, the stent pattern 700 forms sinusoidal hoops or rings 712 that include a group of struts arranged circumferentially. The rings 712 include a series of crests 707 and troughs 709 that alternate with each other. The sinusoidal variation of the rings 712 occurs primarily in the axial direction, not in the radial direction. That is, all points on the outer surface of each ring 712 are at the same or substantially the same radial distance away from the central axis of the stent.

The stent pattern 700 includes various struts 702 oriented in different directions and gaps 703 between the struts. Each gap 703 and the struts 702 immediately surrounding the gap 703 define a closed cell 704. At the proximal and distal ends of the stent, a strut 706 includes depressions, blind holes, or through holes adapted to hold a radiopaque marker that allows the position of the stent inside of a patient to be determined.

One of the cells 704 is shown with cross-hatch lines to illustrate the shape and size of the cells. In the illustrated embodiment, all the cells 704 have the same size and shape. In other embodiments, the cells 704 may vary in shape and size.

Still referring to FIG. 15, the rings 712 are connected to each other by another group of struts that have individual lengthwise axes 713 parallel or substantially parallel to line A-A. The rings 712 are capable of being collapsed to a smaller diameter during crimping and expanded to their original diameter or to a larger diameter during deployment in a vessel. Specifically, pattern 700 includes a plurality of hinge elements 731, 732, 733, 734. When the diameter of a stent having stent pattern 700 is reduced or crimped, the angles at the hinge elements decrease which allow the diameter to decrease. The decrease in the angles results in a decrease in the surface area of the gaps 703. In general, for most coronary applications, the diameter of the scaffold is 2 to 5 mm, or more narrowly 2.5 to 3.5 mm. In general, the length of the scaffold is 8 to 38 mm, or more narrowly, 8 to 12 mm, 12 to 18 mm, 18 mm to 38 mm. The scaffold may be configured for being deployed by a non-compliant balloon, e.g., 2.5 to 4 mm diameter, from about a 1.8 to 2.2 mm diameter (e.g., 2 mm) crimped profile. The coronary scaffold may be deployed to a diameter of between about 2.5 mm and 4 mm.

Exemplary stent scaffold patterns for the SFA are disclosed in application Ser. Nos. 13/015,474 and 13/015,488. As compared to coronary stents, a peripheral (SFA) stent scaffold usually has lengths of between about 36 and 40 mm when implanted in the superficial femoral artery, as an example. The scaffold for SFA may have a pre-crimping diameter of between 7-10 mm, or more narrowly 7-8 mm, and can possess a desired pinching stiffness while retaining at least a 80% recoverability from a 50% crush. The scaffold for SFA may have a wall thickness of about 0.008" to 0.014" and configured for being deployed by a non-compliant balloon, e.g., 6.5 mm diameter, from about a 1.8 to 2.2 mm diameter (e.g., 2 mm) crimped profile. The SFA scaffold may be deployed to a diameter of between about 6.5 mm and 7 mm.

The prevailing mechanism of degradation of many bioabsorbable polymers is chemical hydrolysis of the hydrolytically unstable backbone. In a bulk degrading polymer, the polymer is chemically degraded throughout the entire polymer volume. As the polymer degrades, the molecular weight decreases. The reduction in molecular weight results in changes in mechanical properties (e.g., strength) and stent properties. For example, the strength of the scaffold material and the radial strength of the scaffold are maintained for a period of time followed by a gradual or abrupt decrease. The decrease in radial strength is followed by a loss of mechanical integrity and then erosion or mass loss. Mechanical integrity loss is demonstrated by cracking and by fragmentation. Enzymatic attack and metabolization of the fragments occurs, resulting in a rapid loss of polymer mass.

The behavior of a bioabsorbable stent upon implantation can divided into three stages of behavior. In stage I, the stent provides mechanical support. The radial strength is maintained during this phase. Also during this time, chemical degradation occurs which decreases the molecular weight. In stage II, the scaffold experiences a loss in strength and mechanical integrity. In stage III, significant mass loss occurs after hydrolytic chain scission yields water-soluble low molecular weight species.

The scaffold in the first stage provides the clinical need of providing mechanical support to maintain patency or keep a vessel open at or near the deployment diameter. In some treatments, the patency provided by the scaffold allows the stented segment of the vessel to undergo positive remodeling at the increased deployed diameter. Remodeling refers generally to structural changes in the vessel wall that enhances its load-bearing ability so that the vessel wall in the stented section can maintain an increased diameter in the absence of the stent support. Degradation by-products of the polymer may increase cell growth on and within the scaffold, enhancing remodeling. A period of patency is required in order to obtain permanent positive remodeling.

The degradation of the scaffold results in discontinuities in the scaffold as well as an increase in roughness of the surfaces. Both of these phenomena increase the surface to volume (S/V) ratio of the scaffold, leading to an increase in the cellular growth on the surfaces of the scaffold. The increase in compliance, resulting from both polymer degradation and discontinuities, and the increase in cellular growth reduce or eliminate the incidence of thrombosis during treatment.

The manufacturing process of a bioabsorbable scaffold includes selection of a bioabsorbable polymer raw material or resin. Detailed discussion of the manufacturing process of a bioabsorbable stent can be found elsewhere, e.g., U.S. Patent Publication No. 20070283552. The fabrication methods of a bioabsorbable stent can include the following steps:

(1) forming a polymeric tube from a biodegradable polymer resin using extrusion, (2) radially deforming the formed tube to increase radial strength, (3) forming a stent scaffolding from the deformed tube by laser machining a stent pattern in the deformed tube with laser cutting, in exemplary embodiments, the strut thickness can be 100-200 microns, or more narrowly, 120-180, 130-170, or 140-160 microns, (4) optionally forming a therapeutic coating over the scaffolding, (5) crimping the stent over a delivery balloon, and (6) sterilization with election-beam (E-beam) radiation.

Poly(L-lactide) (PLLA) is attractive as a stent material due to its relatively high strength and rigidity at human body temperature, about 37° C. Since it has a glass transition temperature between about 60 and 65° C. (Medical Plastics and Biomaterials Magazine, March 1998), it remains stiff and rigid at human body temperature. This property facilitates the ability of a PLLA stent scaffold to maintain a lumen at or near a deployed diameter without significant recoil (e.g., less than 10%). In general, the Tg of a semicrystalline polymer can depend on its morphology, and thus how it has been processed. Therefore, Tg refers to the Tg at its relevant state, e.g., Tg of a PLLA resin, extruded tube, expanded tube, and scaffold.

The scaffold can be made of a bioresorbable aliphatic polyester, or a combination thereof. Additional exemplary biodegradable polymers for use with a bioabsorbable polymer scaffolding include poly(D-lactide) (PDLA), polymandelide (PM), polyglycolide (PGA), poly(L-lactide-co-D,L-lactide) (PLDLA), poly(D,L-lactide) (PDLLA), poly(D,L-lactide-co-glycolide) (PLGA) and poly(L-lactide-co-glycolide) (PLLGA). With respect to PLLGA, the stent scaffolding can be made from PLLGA with a mole % of GA between 5-15 mol %. The PLLGA can have a mole % of (LA:GA) of 85:15 (or a range of 82:18 to 88:12), 95:5 (or a range of 93:7 to 97:3), or commercially available PLLGA products identified as being 85:15 or 95:5 PLLGA. The examples provided above are not the only polymers that may be used. Many other examples can be provided, such as those found in Polymeric Biomaterials, second edition, edited by Severian Dumitriu; chapter 4.

Polymers that are more flexible or that have a lower modulus than those mentioned above may also be used. Exemplary lower modulus bioabsorbable polymers include polycaprolactone (PCL), poly(trimethylene carbonate) (PTMC), polydioxanone (PDO), poly(4-hydroxy butyrate) (PHB), and poly(butylene succinate) (PBS), and blends and copolymers thereof.

In exemplary embodiments, higher modulus polymers such as PLLA or PLLGA may be blended with lower modulus polymers or copolymers with PLLA or PLGA. The blended lower modulus polymers result in a blend that has a higher fracture toughness than the high modulus polymer. Exemplary low modulus copolymers include poly(L-lactide)-b-polycaprolactone (PLLA-b-PCL) and poly(L-lactide)-co-polycaprolactone (PLLA-co-PCL). The composition of the blend can include 1-5 wt % of low modulus polymer.

The scaffolds used in the treatments discussed herein may include therapeutic agents, such as antiproliferatives. The scaffolds used in the treatments discussed herein may be coated with one or more therapeutic agents, including an antiproliferative, anti-inflammatory or immune modulating, anti-migratory, anti-thrombotic or other pro-healing agent, or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN™ available from Merck) (synonyms of actinomycin D include dactinomycin, actinomycin IV, actinomycin actinomycin X1, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Other olimus drugs that may be used include, without limitation, Biolimus A9 (Biosensors International, Singapore), deforolimus, AP23573 (Ariad Pharmaceuticals), tacrolimus, temsirolimus, pimecrolimus, novolimus, myolimus, ridaforolimus, 40-O-(3-hydroxy)propyl-rapamycin, 40-O-[2-(2-hydroxy)ethoxy] ethyl-rapamycin, 40-O-tetrazole-rapamycin, 40-epi-(N1-tetrazolyl)-rapamycin (zotarolimus, ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide, nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and combinations thereof. Examples of such cytostatic substances include angiopeptin, and angiotensin converting enzyme inhibitors such as captopril (e.g. Capoten® and Capozide® from Bristol-Myers Squibb Co., Stamford, Conn.), cilazapril and lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable. The scaffold can exclude any of the drugs disclosed herein.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress-strain curve at low strain in the linear region.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. With the preceding discussion in mind, a numerical value herein that is modified by a word of approximation may vary from the stated value by ±15% in some embodiments, by ±10% in some embodiments, by ±5% in some embodiments, or in some embodiments, may be within the 95% confidence interval.

Some non-limiting embodiments of the invention are described by the following numbered paragraphs:

[1] A method of treating coronary heart disease in a patient with diabetes mellitus comprising: deploying a bioabsorbable polymer scaffold at a segment of a coronary artery of a diabetic patient; allowing the deployed bioabsorbable scaffold to provide support to the segment; and allowing the deployed scaffold to resorb from the segment.

[2] The method of paragraph [1], wherein the scaffold comprises a target dose per unit scaffold length of an antiproliferative drug of 8 to 13 µg/mm.

[3] A method of treating coronary heart disease in a patient with diabetes mellitus comprising: deploying a bioabsorbable polymer scaffold in a coronary artery of a diabetic patient, wherein the scaffold comprises a target dose per unit scaffold length of an antiproliferative drug of 8 to 13 µg/mm; and wherein a thickness of struts of the scaffold is greater than 150 microns.

[4] The method of any one of paragraphs [1]-[3], wherein the patient is in need of treatment, prevention, amelioration or a combination thereof, of coronary heart disease.

[5] A method of treating peripheral vascular disease in a patient with diabetes mellitus comprising: deploying a bioabsorbable polymer scaffold at a segment of a peripheral artery of a diabetic patient; allowing the deployed bioabsorbable scaffold to provide support to the segment; and allowing the deployed scaffold to resorb from the segment.

[6] The method of paragraph [5], wherein the scaffold comprises a target dose per unit scaffold length of an antiproliferative drug of 8 to 13 µg/mm.

[7] A method of treating peripheral vascular disease in a patient with diabetes mellitus comprising: deploying a bioabsorbable polymer scaffold in an artery of a diabetic patient, wherein the scaffold comprises a target dose per unit scaffold length of an antiproliferative drug of 8 to 13 µg/mm; and wherein a thickness of struts of the scaffold is greater than 150 microns.

[8] The method of any one of paragraphs [5]-[7], wherein the patient is in need of treatment, prevention, amelioration, or a combination thereof, of peripheral vascular disease.

[9] The method of any one of paragraphs [1]-[8], wherein the scaffold comprises a drug that is delivered from the scaffold to the segment of the artery after deployment.

[10] The method of any one of paragraphs [1]-[9], wherein struts of the scaffold comprise a core and a coating over the core, wherein the core is made of a poly(L-lactide)-based polymer and the coating comprises a polymer and a drug.

[11] The method of paragraph [10], wherein the drug amount in the coating is at least 100 µg/cm$^2$ and not more than 500 µg/cm$^2$.

[12] The method of any one of paragraphs [9]-[11], wherein the drug is everolimus, zotarolimus, or a combination thereof

[13] The method of paragraph [12], wherein the drug is everolimus.

[14] The method of any one of paragraphs [1]-[13], wherein inflation pressure of a delivery balloon during deployment is less than 7 atm.

[15] The method of any one of paragraphs [1]-[14], wherein the rate of balloon expansion of a delivery balloon during deployment is about 6 psi/second or lower.

[16] The method of any one of paragraphs [1]-[15], wherein the scaffold comprises struts with a width greater than 150 microns.

[17] The method of any one of paragraphs [1]-[16], wherein the surface area per scaffold length is at least 8.9 mm$^2$/mm and not more than 30 mm$^2$/mm.

[18] The method of any one of paragraphs [1]-[17], wherein the scaffold comprises a bioresorbable aliphatic polyester.

[19] The method of any one of paragraphs [1]-[18], wherein the scaffold is formed from a biaxially expanded tube made of the polymer.

[20] The method of any one of paragraphs [1]-[19], wherein the scaffold forms a network of rings interconnected by links, including 12 crowns per ring, and at most 2 links connecting substantially all pairs of adjacent rings.

[21] The method of paragraph [20], wherein for any ring of the scaffold there are an equal number of unsupported crowns on each side of each crown connected to a link.

[22] The method of any one of paragraphs [1]-[21], wherein the scaffold provides patency to the segment for at least 3 months.

[23] The method of any one of paragraphs [1]-[22], wherein the scaffold provides patency to the segment for at least 4 months.

[24] The method of any one of paragraphs [1]-[23], wherein the scaffold provides patency to the segment for at least 6 months.

[25] The method of any one of paragraphs [1]-[24], wherein the scaffold is substantially resorbed 2 years after deployment.

[26] The method of any one of paragraphs [1]-[25], wherein the scaffold completely resorbs from the segment, facilitating restoration of natural vasomotion to the segment.

[27] The method of any one of paragraphs [1]-[26], wherein a roughness of surfaces of the scaffold increases with time after implantation which increases a surface area of the surfaces which increases cellular growth on the surfaces.

[28] The method of any one of paragraphs [1]-[27], wherein a compliance of the implanted scaffold increases with time due to discontinuities generated in the scaffold and degradation of the polymer of the scaffold, and wherein the discontinuities in the scaffold increase the surface area to volume (SAT) ratio of the scaffold which increase cellular growth at or near the discontinuities.

[29] The method of paragraph [28], wherein the increase in the compliance and the increase in the cellular growth reduces or eliminates incidence of thrombosis during treatment.

[30] The method of any one of paragraphs [1]-[29], wherein the degradation by-products of the polymer increase cell growth on and within the scaffold.

[31] The method of any one of paragraphs [1]-[30], wherein restenosis of the patient is about the same as that of a non-diabetic patient. In some embodiments, the same as means within a 95% confidence interval, and in further embodiments, the confidence interval is measure using a single-sided comparison to the null hypothesis.

[32] The method of any one of paragraphs [1]-[31], wherein the patient has no thrombosis during at least the first 180 days of the treatment.

[33] The method of any one of paragraphs [1]-[32], wherein the patient has no thrombosis during at least the first 12 months of the treatment.

[34] The method of any one of paragraphs [1]-[33], wherein the percent diameter stenosis, in-segment, is not more than 25% at 180 days of the treatment.

[35] The method of any one of paragraphs [1]-[34], wherein the minimal lumen diameter in mm, in-segment, is about 2.5 mm or less than 2.5 mm, or about 2.2 mm or less than 2.2 mm.

[36] The method of any one of paragraphs [1]-[35], wherein the acute gain in-segment is not less than 0.9 mm.

[37] The method of any one of paragraphs [1]-[36], wherein the incidence of MACE is about the same as that of non-diabetic patients.

[38] The method of any one of paragraphs [1]-[37], wherein a compliance of the scaffold increases with time after deployment, eventually allowing restoration of natural vasomotion to the artery.

[39] The method of any one of paragraphs [1]-[38], wherein the patient is determined to have diabetes mellitus.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating coronary heart disease in a patient with diabetes mellitus comprising deploying a bioabsorbable polymer scaffold at a stenotic segment of a coronary artery of the patient, wherein the deployed scaffold is a network of struts consisting of a core and a coating over the core, wherein the core consists of a poly(L-lactide)-based polymer and the coating consists of poly(DL-lactide) polymer and everolimus drug, wherein the drug is in an amount of at least 100 μg/cm$^2$ and not more than 500 μg/cm$^2$, and wherein the scaffold is fully bioabsorbable and completely absorbs from the segment after a clinical need for the scaffold has ended.

2. The method of claim 1, wherein the scaffold comprises a target dose of the drug per unit scaffold length of 8 to 13 μg/mm.

3. The method of claim 1, wherein the scaffold comprises struts with a width greater than 150 microns.

4. The method of claim 1, wherein the scaffold core is formed from a biaxially expanded tube made of the poly(L-lactide)-based polymer.

5. The method of claim 1, wherein the scaffold is deployed with a delivery balloon having an inflation pressure during deployment that is less than 7 atm.

6. The method of claim 1, wherein the scaffold has a surface area per scaffold length of at least 8.9 mm$^2$/mm and not more than 30 mm$^2$/mm.

7. The method of claim 1, wherein the patient is a non-insulin treated diabetic patient.

8. The method of claim 1, wherein the patient is an insulin treated diabetic patient.

9. The method of claim 1, wherein the scaffold comprises struts with a thickness greater than 150 microns.

10. The method of claim 1, wherein the poly(L-lactide)-based polymer has a tensile modulus of 2 to 7 GPa.

11. A method of treating coronary heart disease in a patient with diabetes mellitus comprising deploying a bioabsorbable polymer scaffold at a stenotic segment of a coronary artery of the patient, wherein the deployed scaffold is a network of struts consisting of a core and a coating over the core, wherein the core consists of a poly(L-lactide)-based polymer and the coating consists of poly(DL-lactide) polymer and everolimus drug, wherein the scaffold is deployed with a delivery balloon having an inflation pressure during deployment that is less than 7 atm, wherein the polymer has a tensile modulus of 2 to 7 GPa, and wherein the scaffold is fully bioabsorbable and completely absorbs from the segment after a clinical need for the scaffold has ended.

12. The method of claim 11, wherein the drug is in an amount of at least 100 µg/cm$^2$ and not more than 500 µg/cm$^2$.

13. The method of claim 11, wherein a target dose per unit scaffold length of the drug is 5 to 15 µg/mm.

14. A method of treating coronary heart disease in a patient with diabetes mellitus comprising deploying a bioabsorbable polymer scaffold at a stenotic segment of a coronary artery of the patient, wherein the deployed scaffold is a network of struts consisting of a core and a coating over the core, wherein the core consists of a poly(L-lactide)-based polymer and the coating consists of poly(DL-lactide) polymer and everolimus drug, wherein the scaffold comprises struts with a thickness greater than 150 microns, wherein the drug has a target dose per unit scaffold length of 5 to 15 µg/mm, and wherein the scaffold is fully bioabsorbable and completely absorbs from the segment after a clinical need for the scaffold has ended.

* * * * *